US007081549B2

(12) United States Patent
Cook et al.

(10) Patent No.: US 7,081,549 B2
(45) Date of Patent: Jul. 25, 2006

(54) PROCESS FOR THE PRODUCTION OF ACETIC ACID

(75) Inventors: John Cook, Sproatley (GB); Brian Ellis, Lower Sunubry (GB); Philip Howard, Kirk Ella (GB); Michael David Jones, Beverley (GB); Simon James Kitchen, Hillam (GB)

(73) Assignee: BP Chemicals Limited, London (GB)

( * ) Notice: Subject to any disclaimer, the term of this patent is extended or adjusted under 35 U.S.C. 154(b) by 113 days.

(21) Appl. No.: 09/797,919

(22) Filed: Mar. 5, 2001

(65) Prior Publication Data
US 2004/0030184 A1 Feb. 12, 2004

Related U.S. Application Data

(63) Continuation of application No. PCT/GB99/02874, filed on Sep. 1, 1999.

(30) Foreign Application Priority Data
Sep. 4, 1998 (GB) .................................. 9819221.4

(51) Int. Cl.
*C07C 51/16* (2006.01)
(52) U.S. Cl. ........................ 562/548; 562/543; 562/544
(58) Field of Classification Search ................ 562/512, 562/606, 607, 608; 560/231, 233, 261
See application file for complete search history.

(56) References Cited

U.S. PATENT DOCUMENTS

| 4,250,346 A | 2/1981 | Young et al. |
| 4,280,929 A | 7/1981 | Shaw et al. |
| 4,328,365 A | 5/1982 | Slinkard et al. |
| 4,677,084 A | 6/1987 | Bergna |
| 4,845,070 A | 7/1989 | Montag |
| 5,210,293 A | 5/1993 | Kitson |
| 5,300,684 A | 4/1994 | Benkalowycz et al. |
| 5,432,141 A | 7/1995 | Brazdil, Jr. et al. |
| 5,466,652 A * | 11/1995 | Paparizos et al. ........... 502/330 |
| 5,591,688 A * | 1/1997 | Blum et al. ................. 502/330 |
| 5,665,667 A | 9/1997 | Lemanski et al. |
| 6,040,474 A * | 3/2000 | Jobson et al. ............... 560/243 |
| 6,194,610 B1 * | 2/2001 | Borchert et al. ............ 562/548 |

FOREIGN PATENT DOCUMENTS

| DE | 196 20 542 A1 | 11/1997 |
| DE | 196 30 832 A1 | 2/1998 |
| DE | 197 17 076 A1 | 10/1998 |
| DE | 197 45 902 A1 | 4/1999 |
| EP | 0 082 222 | 6/1983 |
| EP | 0 407 091 A1 | 1/1991 |
| EP | 0 546 677 A1 | 6/1993 |
| EP | 0 620 205 A1 | 10/1994 |
| EP | 0 672 453 A2 | 9/1995 |
| EP | 0 685 449 A1 | 12/1995 |
| EP | 0 750 942 A2 | 1/1997 |
| EP | 0750942 * | 1/1997 |
| EP | 0 750 942 A2 | 8/1997 |
| GB | 1139210 | 1/1969 |
| JP | 3 245844 | 11/1991 |
| WO | 98/05620 | 2/1998 |
| WO | 99/20592 | 4/1999 |
| WO | 99/51339 | 10/1999 |

OTHER PUBLICATIONS

Derwent Abstract No. 89-210715, Catalyst used in fluidsed bed . . . , XP-002112061.
Japanese Laid Open No. S60 [1985]-220884, Naoto et al (1987).
Abstract No. 95-228499/30, "Silica fine spherical particles, used as . . . ".

* cited by examiner

Primary Examiner—Johann Richter
Assistant Examiner—Karl Puttlitz
(74) Attorney, Agent, or Firm—Nixon & Vanderhye

(57) ABSTRACT

A process for the production of acetic acid, which process comprises contacting ethane and/or ethylene with a molecular oxygen-containing gas in a fluid bed reactor in the presence of a microspheroidal fluidised particulate solid oxidation catalyst, wherein at least 90% of said catalyst particles are less than 300 microns.

19 Claims, No Drawings

PROCESS FOR THE PRODUCTION OF ACETIC ACID

This is a continuation of PCT application No. PCT/GB99/02874, filed 1 Sep. 1999, the entire content of which is hereby incorporated by reference in this application.

The present invention relates to a fluid bed process for the production of acetic acid from ethane and/or ethylene and an oxidation-containing gas.

Processes for the production of acetic acid by the oxidation of ethane and/or ethylene are well known, for example U.S. Pat. No. 4,250,346, EP-A-0407091, DE-A-19620542, DE-A-19630832, and EP-A-0620205.

U.S. Pat. No. 4,250,346 discloses the oxidative dehydrogenation of ethane to ethylene in a gas phase reaction at relatively high levels of conversion, selectivity and productivity at a temperature less than 500° C. using a molybdenum based catalyst.

EP-A-0407091 discloses a process for the production from gaseous ethane and/or ethylene of a product comprising ethylene and/or acetic acid by contacting the feed and a molecular oxygen-containing gas at elevated temperature with a calcined molybdenum/rhenium containing ethane oxidative dehydrogenation catalyst composition.

DE-A-19620542 and DE-A-19630832 disclose a catalyst for the selective oxidation of ethane and/or ethylene to acetic acid which contains molybdenum, palladium and rhenium.

Furthermore GB Patent Application 9807142.6 (BP Case 8979) discloses the use of catalyst comprising molybdenum, tungsten, silver and iridium in the oxidation of ethane to acetic acid.

The process for the production of acetic acid from ethylene and oxygen is also known from EP-A-0620205 wherein ethylene and oxygen are reacted in the presence of a catalyst composition comprising metallic palladium, a heteropolyacid or a salt thereof, and a promoter based on tellurium or selenium salts.

Whilst the above cited prior art states that the process can be carried out in a fixed bed system or a fluidised bed system, the process is only exemplified for the fixed bed system. Operation in a fluidised bed system is generally undesirable due to process difficulties, in particular catalyst attrition.

We have now found that the problem of catalyst attrition can be overcome for a fluidised system through the use of a microspheroidal particulate catalyst material.

Accordingly, the present invention provides a process for the production of acetic acid which process comprises contacting ethane and/or ethylene with a molecular oxygen-containing gas in a fluid bed reactor in the presence of a microspheroidal fluidised particulate solid oxidation catalyst, wherein at least 90% of said catalyst particles are less than 300 microns.

The present invention provides a process for the production of acetic acid in a fluidised reactor through the use of specific particulate catalyst materials. The use of the specific catalyst overcomes operational problems previously experienced in fluid bed processes.

The process of the present invention requires a microspheroidal particulate catalyst. It is required that at least 90% of the particles are less than 300 microns, preferably at least 95% of the particles are less than 300 microns. Suitably, the particle size distribution may be as follows:

| | |
|---|---|
| 0–20 microns | 0.30 wt % |
| 20–44 microns | 0–60 wt % |
| 44–88 microns | 10–80 wt % |
| 88–106 microns | 10–80 wt % |
| >106 microns | 0–40 wt % |
| >300 microns | 0–5 wt % |

Suitably, the catalyst has a density of from 0.5 to 5 g/cm², preferably 1 to 3 g/cm³, especially 1.5 to 2 g/cm³.

The catalyst is used in a fluid bed reactor, it is preferred that the catalyst particles be attrition resistant.

Catalyst suitable for use in the fluid bed process for the conversion of ethane are conventional ethane oxidation catalysts, provided such catalysts are used in the microspheroidal particulate form.

Suitable catalysts include a catalyst composition comprising molybdenum e.g. $Mo_a X_b Y_c$ wherein
  X is Cr, Mn, Nb, Ta, Ti, V and/or W, and preferably Mn, Nb, V and/or W
  Y is Bi, Ce, Co, Cu, Fe, K, Mg, Ni, P, Pb, Sb, Si, Sn, Tl and/or U, and preferably Sb, Ce and/or U,
  a is 1,
  b is 0.05 to 1.0 and
  c is 0 to 2, and preferably 0.05 to 1.0, with the proviso that the total value of c for Co, Ni and/or Fe is less than 0.5.

Equally suitable is catalyst composition $Mo_d Re_e W_g XY$ wherein
  $A = Mo_d Re_e W_f$,
  X=Cr, Mn, Nb, Ta, Ti, V and/or W, and preferably Mn, Nb, V and/or W,
  Y=Bi, Ce, Co, Cu, Fe, K, Mg, Ni, P, Pb, Sb, Si, Sn, Tl and/or U, and preferably Sb, Ce and/or U,
  a=1,
  b=0 to 2, preferably 0.05 to 1.0,
  c=0 to 2, preferably 0.001 to 1.0, and more preferably 0.05 to 1.0 with the proviso that the total value of c for Co, Ni, and/or Fe is less than 0.5,
  d+e+f=a,
  d is either zero or greater than zero,
  e is greater than zero, and
  f is either zero or greater than zero.

Also possible is catalyst composition $Mo_a Pd_b Re_c X_d Y_e$ wherein
  X=Cr, Mn, Nb, B, Ta, Ti, V and/or W
  Y=Bi, Ce, Co, Cu, Te, Fe, Li, K, Na, Rb, Be, Mg, Ca, Sr, Ba, Ni, P, Pb, Sb, Si, Sn, Tl and/or U;

the indices a, b, c, d and e stand for the gram atom ratios of the corresponding elements, where a=1, b>0, c>0, d=0.05 to 2 and e=0 to 3.

A further suitable catalyst is $Mo_a Pd_b X_c Y_d$ wherein
  X stands for one or more of the elements selected from the group Cr, Mn, Nb, Ta, Ti, V and W;
  Y stands for one or more of the elements selected from the group B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Zr, Hf, Ni, P, Pb, Sb, Si, Sn, Ti, and U;

the indices a, b, c, d stand for the gram atom ratios of the corresponding elements, where
  a=1; b>0; c>0 and d=0–2.
A further suitable oxide catalyst is $Mo_aW_bAg_cIr_dX_eY_f$
wherein
  X is the elements Nb and V
  Y is one or more elements selected from the group Cr, Mn, Ta, Ti, B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Zr, Hf, Ni, P, Pb, Sb, Si, Sn, Tl, U, Re and Pd;
  a, b, c, d, e and f represent the gram ratios of elements such that
  $0<a\leq 1$, $0\leq b<1$ and a+b=1
  $0<(c+d)\leq 0.1$; $0<e\leq 2$ and $0\leq f\leq 2$ Suitable catalysts for the conversion of ethane to acetic acid are MoAg VNb and a composition comprising with oxygen, the elements molybdenum, vanadium, niobium and gold.

Where the feed comprises ethylene and the molecular oxygen-containing gas, catalysts suitable for use in the process of the present invention comprise a composition of metallic palladium and a heteropoly-acid or salt thereof. The heteropoly acid may contain one hetero atom or one or more polyatoms. The hetero atom may suitably be phosphorus, silicon, boron, aluminium, germanium, titanium, zirconium, cerium, cobalt, chromium, or sulphur. The poly atom may suitably be molybdenum, tungsten, vanadium, niobium or tantalum.

Examples of the heteropoly-acids may include silicotungstic acid, phosphotungstic acid, phosphomolybdic acid, silicomolybdic acid, tungstomolybdophosphoric acid, tungstomolybdosilisic acid, tungstovanadophosphoric acid, tungstovanadosilisic acid, molybdovanadophosphoric acid, molybdovanadosilisic acid, borotungstic acid, boromolybdic acid, tungstomolybdoboric acid, molybdoalumrinic acid, tungstoaluminic acid, molybdotungstoaluminic acid, molybdogermanic acid, tungstogermanic acid, molybdotungstogermanic acid, molybdotitanic acid, tugnstotitanic acid, molybdotungstotitanic acid, cericmolybdic acid, cerictungstic acid, cericmolybdotungstic acid, molybdocobalt acid, tungstocobalt acid, molybdotungstocobalt acid, phosphoniobic acid, siliconiobic acid and silicotantalic acid. Among them, silicotungstic acid, phosphotungstic acid, phosphomolybdic acid, silicomolybdic acid, tungstomolybdophosphoric acid, tungstomolybdosilisic acid, tungstovanadophosphoric acid, tungstovanadosilisic acid, molybdovanadosilisic acid, borotungstic acid, boromolybdic acid and boromolybdotungstic acid are especially preferred.

The salts of heteropoly-acids may be metal or onium salts in which the hydrogen atoms or an acid formed by condensing two or more inorganic oxygen acid are partially or entirely substituted by one or more metal or onium cations. The metals by which the hydrogen atoms of the heteropoly-acids are substituted are selected from the group consisting of the metals of the Groups 1(1A), 2(2A), 11(1B) and 13(3B) of the Long-Form Periodic Table such as alkali metals, alkaline earth metals, copper, silver, gold, aluminium, gallium, indium and thallium. As examples of the onium salts, there may be mentioned ammonium salts derived from ammonia or an amine. Among the heteropoly-acid salts, lithium, sodium, potassium, cesium, magnesium, barium, copper, gold and galliume salts are especially preferred, with the most preferred examples being lithium, sodium and copper salts of phosphotungstic acid and lithium, sodium and copper salts of silicotungstic acid.

The proportion of palladium to heteropoly acid in the catalyst composition is suitably 1 g atom:0.025 to 500 g molecules, preferably 1 g atom:0.1 to 400 g molecules.

The catalyst composition may also suitably comprise a metal selected from Group IB, IVB, VB and VIB of the Periodic Table. Suitable metals include, copper, silver, tin, lead, antimony, bismuth, selenium, and tellurium. Where the metal is present, the proportion of palladium to heteropoly-acid to metal is suitably from 1 g atom:0.025 to 500 g molecules:0.005 to 10 g atoms, preferably 1 g atom:0.1 to 400 g molecules:0.01 to 5 g atoms.

The preferred catalyst for the production of acetic acid from ethylene and an oxygen-containing gas is a three component system comprising (1) metallic palladium, (2) phosphotungstic acid, silicotungstic acid or at least one of lithium, sodium, and copper salts of phosphotungstic acid and lithium, sodium and copper salts of silicotungstic acid; and (3) at least one of bismuth, selenium and tellurium.

Suitably, the catalyst for conversion of ethane and/or ethylene comprises a binder material which may be silica, titania, alumina, zirconia or a mixture thereof. Suitably, the binder material is present in a concentration of at least 10 wt % of the catalyst composition.

The catalyst composition may be prepared by any of the methods conventionally employed for the preparation of fluid bed catalysts. As regards the ethane oxidation catalyst, the catalyst may suitably be prepared by spray drying a slurry of the binder material, e.g. a silica sol, a complex or compound of the elements e.g. oxides and water. The catalyst particles may then calcined by heating to a temperature of between 300 and 800° C., suitably in air or oxygen for a period of 1 minute to 24 hours. Preferably the air or oxygen is free flowing.

With regard to the preparation of the ethylene oxidation catalyst such as palladium heteropolyacid catalyst, again this may be prepared by conventional methods. Suitably, the catalyst may be prepared by dissolving the palladium compound and the metal compound in a suitable solvent, The carrier or binder material may be added to the solution. The resulting solution may be dried to provide the catalyst. Alternatively, the catalyst may be precipitated by the addition of a precipitating medium. The resulting compound is then suitably reduced by a reducing agent such as hydrogen or hydrazine. Alternatively, the catalyst may be prepared by spray drying the desired support. Palladium may then be added by wet impregnation and the resulting compound dried. The dried product may then be reduced with a suitable reducing agent.

The feed gas comprises ethane and/or ethylene. Ethane and ethylene may be used in substantially pure form or admixed with nitrogen, methane, carbon dioxide, or water in the form of steam which may be present in major amounts, for example greater than 5 volume percent. Such gases may be added as fresh gases or may be introduced as a recycle gas stream. Hydrogen, carbon monoxide, $C_3/C_4$ alkanes and alkenes may also be present in minor amounts, for example less than 5 volume percent.

The molecular oxygen-containing gas may be air or a gas richer or poorer in molecular oxygen than air, for example oxygen. A suitable gas may be, for example, oxygen diluted with a suitable diluent, for example nitrogen.

Optionally, water (steam) may be fed into the reactor with the ethane and/or ethylene and the molecular oxygen-containing gas.

The process may generally be carried out at a temperature in the range from 130 to 500° C., preferably from 140 to 400° C.

The pressure may be suitably atmospheric or superatmospheric, for example from 1 to 50 bara, preferable from 1 to 30 bara.

In a preferred embodiment, the process of the present invention may be the first step in an integrated process for the production of acetic acid and/or vinyl acetate such as that described, for example, in International patent publication WO 98/05620, the contents of which are incorporated herein by reference. Thus, according to this embodiment, there is provided an integrated process for the production of acetic acid and/or vinyl acetate which comprises the steps (a) contacting in a first reaction zone a feedstock comprising ethylene and/or ethane and optionally steam with a molecular oxygen-containing gas in the presence of a catalyst active for the oxidation of ethylene to acetic acid and/or ethane to acetic acid and ethylene as hereinbefore described, to produce a first product stream comprising acetic acid, water and ethylene (either as unreacted ethylene and/or as co-produced ethylene) and optionally also ethane, carbon monoxide, carbon dioxide and/or nitrogen; and (b) contacting in a second reaction zone in the presence or absence of additional ethylene and/or acetic acid at least a portion of the first gaseous product stream comprising at least acetic acid and ethylene and optionally also one or more of water, ethane, carbon monoxide, carbon dioxide and/or nitrogen with a molecular oxygen-containing gas in the presence of a catalyst active for the production of vinyl acetate to produce a second product stream comprising vinyl acetate, water, acetic acid and optionally ethylene.

Preferably the integrated process comprises the further steps of:

(c) separating the product stream from step (b) by distillation into an overhead azeotrope fraction comprising vinyl acetate and water and a base fraction comprising acetic acid; and (d) either
  (i) recovering acetic acid from the base fraction separated in step (c) and optionally recycling the azeotrope fraction separated in step (c) after partial or complete separation of the water therefrom to step (c),
  or (ii) recovering vinyl acetate from the azeotrope fraction separated in step (c) and optionally recycling the base fraction separated in step (c) to step (b),
  or (iii) recovering acetic acid from the base fraction separated in step (c) and recovering vinyl acetate from the overhead azeotrope fraction recovered in step (c).

The catalyst and processes of the present invention will now be further illustrated by reference to the following Examples.

PREPARATION OF CATALYST (1) Ethane Oxidation Catalyst

The fluid bed ethane oxidation catalyst consists of a number of elements incorporated into an attrition resistant silica-based microspheroidal fluid bed support. The microspheroidal catalyst is prepared by spray drying a slurry consisting of a mixture of silica sol, ammonium molybdate, silver acetate, ammonium vanadate, niobium chloride and oxalic and water, to give a target catalyst composition of $Mo_{0.72}Ag_{0.01}V_{0.18}Nb_{0.09}$. The microspheroids are then calcined in air between 400° C. to decompose salts and to give strength (attrition resistance) to the catalyst. The proportion of the above elements in the finished catalyst was 50 wt %, the proportion of silica in the finished catalyst was thus 50 wt %.

Catalyst Properties

Particle Size Distribution:

| | |
|---|---|
| 0–20 microns | 0–30 wt % |
| 20–44 microns | 0–60 wt % |
| 44–88 microns | 10–80 wt % |
| 88–106 microns | 10–80 wt % |
| >106 microns | 0–40 wt % |
| >300 microns | 0–5 wt % |
| Density | 0.5–3.0 g/cm$^2$ |

The catalyst prepared was found to have the composition $Mo_{0.73}Ag_{0.01}V_{0.18}Nb_{0.08}$ pre-calcination.

(2) Ethylene Oxidation Catalyst $Na_2PdCl_4$ (1.5829 g) was dissolved in de-ionised water (20 g) and then reverse impregnated (addition of solid to solution) onto spray-dried silica support (29.99 g, 17500-39B, av. 70 micron diameter). The resulting solid was dried for 16 hours at room temperature and pressure. $NH_2NH_2$ hydrate (3.33 g) was added to de-ionised water (80 g). The dried solid was added slowly to the hydrazine solution. The mixture was allowed to stand for 16 hours at room temperature and pressure with occasional swirling. The solution was suction filtered to separate the solid from the filtrate and then washed with de-ionised water (4×125 ml) after which the filtrate gave a negative result when tested for presence of chloride. The solid was dried for 40 hours at room temperature and pressure to give the reduced palladium catalyst intermediate. $KSeO_4$ (0.246 g) was dissolved in de-ionised water (20 g) and reverse impregnated onto the reduced palladium catalyst intermediate solid, which was then dried for 16 hours at room temperature and pressure. $H_4SiO_4.12WO_3.xH_2O$ (9.45 g) was dissolved in de-ionised water and reverse impregnated onto the dried solid, which was then re-dried for 40 hours at 60° C. The resulting catalyst was activated prior to use by heating for 4 hours at 200° C.

Acetic Acid Production

A 40 ml fluidised bed heterogeneous reactor was operated at 8 barg within a vessel through which heat transfer fluid was circulated. The reactants were fed in vapour phase, via a sintered element, into the base of the reactor to fluidise the catalyst. There was provision to mass flow control additional oxygen and/or nitrogen to the reactor from the same source as the main gas feeds. The pressure was maintained by a back pressure control valve on the common exit from the reactor. The reactor temperature was maintained by the circulating heat transfer fluid which was heated by a Haake bath. A multi-point thermocouple measured the reactor temperature. This reactor was used for a series of fluid bed experiments testing for the production of acetic acid from ethane and/or ethylene and an oxygen-containing gas. The reaction conditions are given in Tables 1 and 2.

On-line gas chromatograph analysis of the composition of the outlet stream allowed space time yield calculations for the production of acetic acid to be calculated. This analysis did not include calculation of ethylene co-production.

For each fluid bed experiment the reactor was charged with catalyst or catalyst/diluent* mixture and then sealed and tested under pressure with nitrogen. Once at steady reaction temperature and pressure, the reactant stream was introduced sequentially (hydrocarbon, steam, oxygen), each time allowing the fluid bed to stabilise. Once at steady operating conditions, the experiment was run for >12 hours, analysis via on-line gas chromatography could be collected as frequently as every ½ hour. *non-impregnated spray-dried silica It can be seen from the results in Tables 3 and 4 that acetic acid is produced from ethane and ethylene using the fluidised particulate catalyst.

TABLE 1

Reaction Conditions for Ethane Oxidation to Acetic Acid

| Example | 1 | 2 | 3 |
|---|---|---|---|
| REAC TEMP ° C. | 190.00 | 200.00 | 215.00 |
| PRESSURE barg | 8.00 | 8.00 | 8.00 |
| CAT Wt (g) | 28.495 | 28.495 | 28.495 |
| DIL Wt (g) | nil | nil | nil |
| ethane mol % | 48.53 | 48.53 | 48.53 |
| oxygen mol % | 27.17 | 27.17 | 27.17 |
| nitrogen mol % | 6.59 | 6.59 | 6.59 |
| water mol % | 17.72 | 17.72 | 17.72 |
| TOTAL FLOW (ml/min) | 425.90 | 425.90 | 425.90 |

TABLE 2

Reaction Conditions for Ethylene Oxidation to Acetic Acid

| Example | 5 | 6 |
|---|---|---|
| REAC TEMP ° C. | 160.00 | 160.00 |
| PRESSURE barg | 8.00 | 8.00 |
| CAT Wt (g) | 14.29 | 29.50 |
| DIL Wt (g) | 12.21 | nil |
| ethylene mol % | 39.93 | 39.47 |
| oxygen mol % | 6.63 | 6.56 |
| nitrogen mol % | 24.91 | 24.63 |
| water mol % | 28.53 | 29.35 |
| TOTAL FLOW (ml/min) | 357.04 | 361.18 |

Results:

TABLE 3

Space Time Yield (AcOH) Calculations for Ethane Oxidation to Acetic Acid

Example 1

| Hours on stream | 11.5 | 12 | 13.5 | 15 | 17 | 17.5 | 20.5 | 21.5 | | |
|---|---|---|---|---|---|---|---|---|---|---|
| STY | 149.20 | 77.55 | 135.55 | 132.19 | 145.05 | 112.78 | 159.92 | 141.21 | | |

Example 2

| Hours on stream | 32.5 | 34.5 | 35.5 | 36 | 38 | 39 | 41 | 43.5 | 44.5 | 46 |
|---|---|---|---|---|---|---|---|---|---|---|
| STY | 192.81 | 216.07 | 136.52 | 216.57 | 190.69 | 229.20 | 199.17 | 156.29 | 207.57 | 166.28 |

Example 3

| Hours on stream | 1 | 2 | 3 | 4 | 9 | 12 | 14 | 17 | 22 | |
|---|---|---|---|---|---|---|---|---|---|---|
| STY | 328.11 | 321.75 | 326.32 | 297.14 | 354.40 | 331.19 | 337.34 | 300.20 | 317.79 | |

TABLE 4

Space Time Yield (AcOH) Calculations for Ethylene Oxidation to Acetic Acid

Example 5

| Hours on stream | 1 | 3 | 5 | 9 | 11 | 13 |
|---|---|---|---|---|---|---|
| STY | 91.40 | 65.62 | 85.63 | 66.07 | 45.21 | 65.78 |

Example 6

| Hours on stream | 1 | 3 | 5 | 7 | 11 | 13 |
|---|---|---|---|---|---|---|
| STY | 258.52 | 184.96 | 149.04 | 142.73 | 102.20 | 115.80 |

The invention claimed is:

1. A process for the production of acetic acid which process comprises contacting ethane and/or ethylene with a molecular oxygen-containing gas in a fluid bed reactor in the presence of a microspheroidal fluidised particulate solid oxidation catalyst, wherein at least 90% of said catalyst particles are less than 300 microns.

2. A process as claimed in claim 1 wherein at least 95% of the catalyst particles are less than 300 microns.

3. A process as claimed in claim 1 wherein ethane is contacted with a catalyst comprising molybdenum.

4. A process as claimed in claim 3 whereas the catalyst is $Mo_aW_bAg_cIr_dX_eY_f$ wherein X is selected from the group elements Nb and V Y is one or more elements selected from the group consisting of Cr, Mn, Ta, Ti, B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Zr, Hf, Ni, P, Pb, Sb, Si, Sn, Tl, U, Re and Pd;

a, b, c, d, e and f represent the gram ratios of elements such that $0<a\leq1$, $0\leq b<1$ and $a+b=1$ $0<(c+d)\leq0.1$ $0<e\leq2$ and $0<f\leq2$.

5. A process as claimed in claim 1 or claim 2 wherein ethylene is contacted with a catalyst composition comprising metallic palladium, and a heteropoly-acid or salt thereof.

6. A process as claimed in claim 5 wherein the catalyst composition comprises a metal selected from Group IB, IVB, VB and VIB of the Periodic Table.

7. A process as claimed in claim 6 wherein the metal is selected from copper, silver, tin, lead, antimony, bismuth, selenium and tellurium.

8. A process as claimed in claim 5 wherein the catalyst comprises (1) metallic palladium, (2) phosphotungstic acid, silicotungstic acid or at least one of the lithium sodium or copper salts thereof; (3) at least one of bismuth, selenium and tellurium.

9. A process as claimed in claim 1 wherein the catalyst comprises a binder material selected from the group silica, titania, alumina, zirconia, or a mixture thereof in a concentration of at least 10 wt % of the catalyst composition.

10. A process as claimed claim 1 carried out at a temperature of 130 to 500° C.

11. A process as claimed in claim1 carried out under a pressure of 1 to 50 bara.

12. An integrated process for the production of acetic acid and/or vinyl acetate which comprises:
 (a) contacting in a first reaction zone a feedstock comprising ethylene and/or ethane and optionally steam with a molecular oxygen-containing gas in the presence of a microspheroidal fluidised particulate solid oxidation catalyst wherein at least 90% of said catalyst particles are less than 300 microns for the oxidation of ethylene to acetic acid and/or ethane to acetic acid to produce a first product stream comprising acetic acid, water and ethylene (either as unreacted ethylene and/or as co-produced ethylene) and optionally also ethane, carbon monoxide, carbon dioxide and/or nitrogen; and
 (b) contacting in a second reaction zone in the presence or absence of additional ethylene and/or acetic acid at least a portion of the first gaseous product stream comprising at least acetic acid and ethylene and optionally also one or more of water, ethane, carbon monoxide, carbon dioxide and/or nitrogen with a molecular oxygen-containing gas in the presence of a catalyst active for the production of vinyl acetate to produce a second product stream comprising vinyl acetate, water, acetic acid and optionally ethylene.

13. An integrated process as claimed in claim 12 which comprises the further steps of:
 (c) separating the product stream from step (b) by distillation into an overhead azeotrope fraction comprising vinyl acetate and water and a base fraction comprising acetic acid; and
 (d) either (i) recovering acetic acid from the base fraction separated in step (c) and optionally recycling the azeotrope fraction separated in step (c) after partial or complete separation of the water therefrom to step (c),
 or (ii) recovering vinyl acetate from the azeotrope fraction separated in step (c) and optionally recycling the base fraction separated in step (c) to step (b),
 or (iii) recovering acetic acid from the base fraction separated in step (c) and recovering vinyl acetate from the overhead azeotrope fraction recovered in step (c).

14. A process as claimed in claim 3 wherein the catalyst comprises a binder material selected from the group consisting of silica, titania, alumina, zirconia, and a mixture thereof in a concentration of at least 10 wt % of the catalyst composition.

15. A process as claimed in claim 4 wherein the catalyst comprises a binder material selected from the group consisting of silica, titania, alumina, zirconia, and a mixture thereof in a concentration of at least 10 wt % of the catalyst composition.

16. A process as claimed in claim 5 wherein the catalyst comprises a binder material selected from the group consisting of silica, titania, alumina, zirconia, and a mixture thereof in a concentration of at least 10 wt % of the catalyst composition.

17. A process as claimed in claim 6 wherein the catalyst comprises a binder material selected from the group consisting of silica, titania, alumina, zirconia, and a mixture thereof in a concentration of at least 10 wt % of the catalyst composition.

18. A process as claimed in claim 7 wherein the catalyst comprises a binder material selected from the group consisting of silica, titania, alumina, zirconia, and a mixture thereof in a concentration of at least 10 wt % of the catalyst composition.

19. A process as claimed in claim 8 wherein the catalyst comprises a binder material selected from the group consisting of silica, titania, alumina, zirconia, and a mixture thereof in a concentration of at least 10 wt % of the catalyst composition.

* * * * *